(12) United States Patent
Van et al.

(10) Patent No.: US 7,048,925 B2
(45) Date of Patent: *May 23, 2006

(54) ACID-SENSITIVE POLYACETALS AND METHODS

(75) Inventors: Sang Van, San Diego, CA (US); Nitnara Viroonchatapan, Oceanside, CA (US); Shouping Ji, Vista, CA (US); Lei Yu, Carlsbad, CA (US)

(73) Assignee: Nitto Denko Corporation (JP)

( * ) Notice: Subject to any disclaimer, the term of this patent is extended or adjusted under 35 U.S.C. 154(b) by 329 days.

This patent is subject to a terminal disclaimer.

(21) Appl. No.: 10/651,394

(22) Filed: Aug. 28, 2003

(65) Prior Publication Data

US 2005/0049387 A1 Mar. 3, 2005

(51) Int. Cl.
*A61K 39/44* (2006.01)
*C08F 283/00* (2006.01)

(52) U.S. Cl. .................... 424/178.1; 528/332; 528/363; 528/364; 528/376; 528/392; 528/422; 528/425; 525/535; 525/540; 514/579; 514/609; 514/613; 514/716; 514/722; 514/723; 424/1.53; 424/179.1; 530/391.5; 530/402

(58) Field of Classification Search ................. 528/332, 528/363, 364, 376, 392, 422, 425; 525/535, 525/540; 514/579, 609, 613, 716, 722, 723; 424/178.1, 1.53, 179.1; 530/391.5, 402
See application file for complete search history.

(56) References Cited

U.S. PATENT DOCUMENTS 4,713,441 A 12/1987 Heller et al.
(Continued)

FOREIGN PATENT DOCUMENTS

EP 0 949 905 B1 7/2001
(Continued)

OTHER PUBLICATIONS

Ahn, Cheol–Hee et al., "Biodegradable poly(ethylenimine) for plasmid DNA delivery," Journal of Controlled Release 80 (2002), pp. 273–282.
(Continued)

*Primary Examiner*—Samuel A. Acquah
(74) *Attorney, Agent, or Firm*—Knobbe Martens Olson & Bear LLP

(57) ABSTRACT

Polyacetals comprising a recurring units represented by a formula selected from the group consisting of formula (I) and (II):

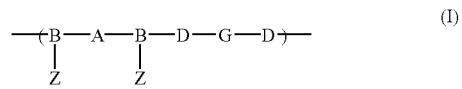

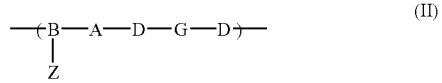

wherein A comprises at least one acetal group; B is selected from the group consisting of —CH—, —CH(CH$_3$)—, CH$_2$CH—, —CH$_2$C(CH$_3$)—, —CH(CH$_3$)CH—, and —CHCH(CH$_3$)CH(CH$_3$)—; Z is selected from the group consisting of C(O)OR$^1$, C(O)SR$^1$, C(O)NR$^1$R$^2$, and VU; V is a linker group; U is selected from the group consisting of poly(ethyleneimine), poly(propyleneimine), poly(lysine), PAMAM dendrimer, octaamine dendrimer, hexadecaamine dendrimer, enhancer, and targeting receptor; R$^1$ and R$^2$ are each individually selected from the group consisting of hydrogen, C$_1$ to C$_{10}$ alkyl, and C$_6$ to C$_{10}$ aryl; D is a linkage selected from the group consisting of carboxylic amide, carboxylic ester, urea, and urethane; and G is selected from the group consisting of C$_4$ to C$_{20}$ alkyl, C$_6$–C$_{10}$ aryl, and —(OCH$_2$CH$_2$)$_n$—, where n is in the range of 1 to about 250, are useful in nucleic acid delivery applications. In preferred embodiments, complexes formed between polyacetals of the formulae (I) or (II) and polynucleotides are useful as transfection reagents.

42 Claims, 11 Drawing Sheets

U.S. PATENT DOCUMENTS

| | | |
|---|---|---|
| 5,958,398 A | 9/1999 | Papisov et al. |
| 6,331,311 B1 | 12/2001 | Brodbeck et al. ............ 424/425 |
| 2002/0034532 A1 | 3/2002 | Brodbeck et al. ............ 424/422 |

FOREIGN PATENT DOCUMENTS

| | | |
|---|---|---|
| WO | WO 92/11844 | 7/1992 |
| WO | WO 98/27962 | 7/1998 |
| WO | WO 98/27963 | 7/1998 |
| WO | WO 02/15955 A2 | 2/2002 |
| WO | WO 02/20633 | 3/2002 |
| WO | WO 02/20663 A2 | 3/2002 |
| WO | WO 02/49573 A2 | 6/2002 |

OTHER PUBLICATIONS

Basko, M. et al., "Synthesis of Double Hydrophilic Graft Copolymers with a Polyacetal Backbone," Macromolucules, 2002, 35, pp. 8948–8953.

Brazeau, Gayle A., "In Vitro Myotoxicity of Selected Cationic Macromolecules Used in Non–Viral Gene Delivery," Pharmaceutical Research, vol. 15, No. 5, 1998, pp. 680–684.

Carpino, L.A. et al.; "The 9–Fluorenylmethoxycarbonyl Amino–Protecting Group," J. Org. Chem., 1972, 37, pp. 3404–3409.

Choksakulnimitr, Suthummar et al., "In vitro cytotoxicity of macromolecules in different cell culture systems," Journal of Controlled Release 34 (1995) pp. 233–241.

Godbey, W.T. et al.; "Size matters: Molecular weight affects the effciency of poly(ethylwnimine) as a gene delivery vehicle," J. Biom. Mat. Res. Part A., 1999, 45, pp. 268–275.

Lim, Yong–Beom et al., "Biodegradable Polyester, Poly [α–4–Aminobutyl)–L–Glycolic Acid], as a Non–Toxic Gene Carrier," Pharmaceutical Research, vol. 17, No. 7, 2000, pp. 811–816.

Lim, Yong–Beom et al., "Biodegradable, Endosome Disruptive, and Cationic Network–type Polymer as a Highly Efficient and Nontoxic Gene Delivery Carrier," Bioconjugate Chem. 2002, 13, pp. 952–957.

Lim, Yong–Beom et al., "Cationic Hyperbranched Poly(amino ester): A Novel Class of DNA Condensing Molecule with Cationic Surface, Biodegradable Three–Dimensional Structure, and Teriary Amine Groups in the Interior," Journal of American Chemical Society 2001, 123, pp. 2460–2461.

Luo, Dan et al., "Synthetic DNA delivery systems," Nature Biotechnology, vol. 18, Jan. 2000, pp. 33–37.

Lynn, David M. et al., "Accelerated Discovery of Synthetic Transfection Vectors: Parallel Synthesis and Screening of a Degradable Polymer Library," Journal American Chemical Society 2001, 123, pp. 8155–8156.

Mulligan, Richard C., "The Basic Science of Gene Therapy," Science, vol. 260, May 14, 1993, pp. 926–932.

Murthy, Niren et al., "A Novel Strategy for Encapsulation and Release of Proteins: Hydrogels and Microgels with Acid–Labile Acetal Cross–Linkers," Journal American Chemical Society 2002, 124, pp. 12398–12399.

Tomlinson, Ryan et al., "Pendent Chain Functionalized Polyacetals That Display pH–Dependent Degradation: A Platform for the Development of Novel Polymer Therapeutics," Macromolecules 2002, 35, pp. 473–480.

Torres, L.F. et al.: "A New Polymerization System for Bicyclic Acetals: Toward the Controlled/"Living" Cationic Ring–Opening Polymerization of 6.8–Dioxabicyclo[3.2.1] octane," Macromolecules, 1999, 32, pp. 6958–6962.

Tuominen, Jukka et al., "Biodegradation of Lactic Acid Based Polymers under Controlled Composting Conditions and Evaluation of the Ecotoxicological Impact," Biomacromolecules 2002, 3, pp. 445–455.

U.S. Appl. No. 10/375,705, filed Feb. 25, 2003.

International Search Report for International Application No. PCT/US2004/024284 dated Nov. 19, 2004.

Lee, E.S., et al., "Poly(L–histidine)–PEG block copolymer micelles and pH–induced destabilization," Journal of Controlled Release, vol. 90, Jul. 31, 2003, pp. 363–374.

Murthy, N. et al., "Design and synthesis of pH–responsive polymeric carriers that target uptake and enhance the intracellular delivery of oligonucleotides," Journal of Controlled Release, vol. 89, May 20, 2003, pp. 365–374.

FIGURE 4
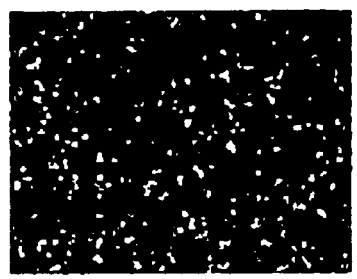
49
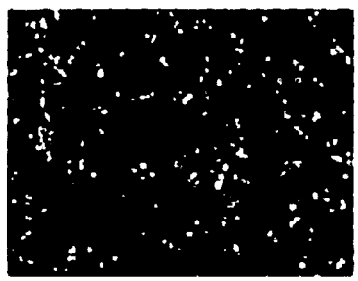
48
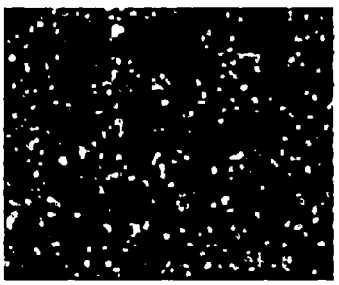
47
46
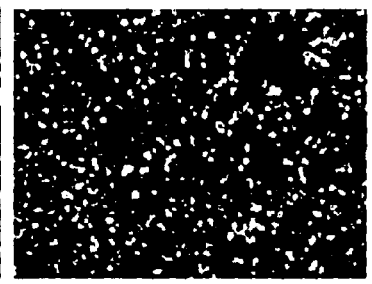
51
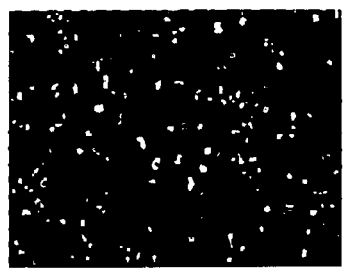
50
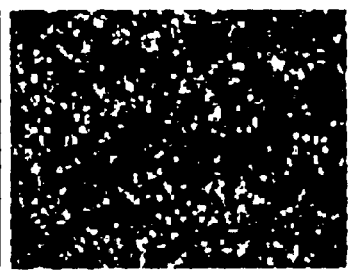
L2000
PEI-1800

FIGURE 7

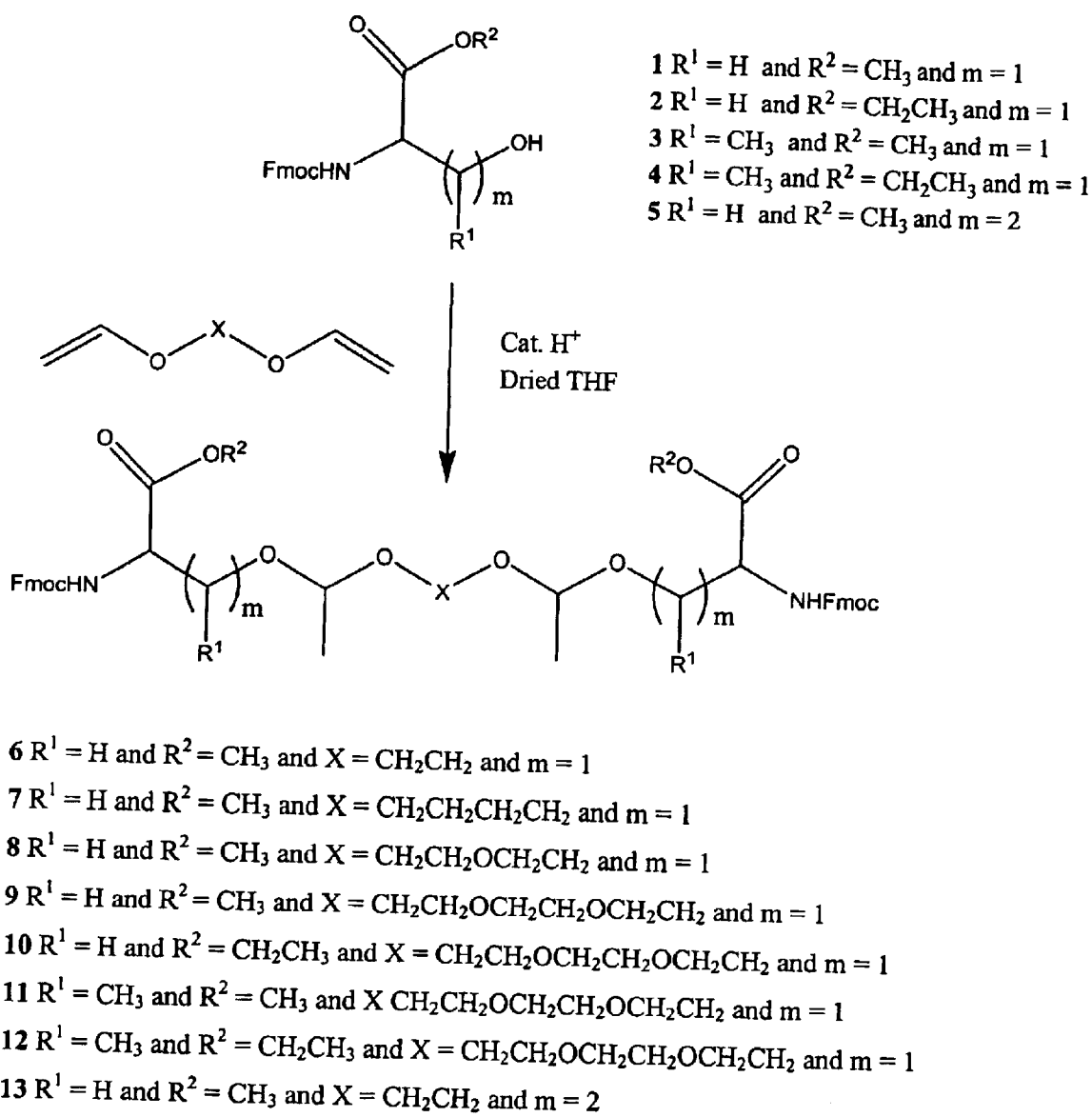

1  $R^1 = H$  and  $R^2 = CH_3$  and  m = 1
2  $R^1 = H$  and  $R^2 = CH_2CH_3$ and  m = 1
3  $R^1 = CH_3$  and  $R^2 = CH_3$  and  m = 1
4  $R^1 = CH_3$  and  $R^2 = CH_2CH_3$ and  m = 1
5  $R^1 = H$  and  $R^2 = CH_3$  and  m = 2

6  $R^1 = H$ and $R^2 = CH_3$ and $X = CH_2CH_2$ and m = 1
7  $R^1 = H$ and $R^2 = CH_3$ and $X = CH_2CH_2CH_2CH_2$ and m = 1
8  $R^1 = H$ and $R^2 = CH_3$ and $X = CH_2CH_2OCH_2CH_2$ and m = 1
9  $R^1 = H$ and $R^2 = CH_3$ and $X = CH_2CH_2OCH_2CH_2OCH_2CH_2$ and m = 1
10 $R^1 = H$ and $R^2 = CH_2CH_3$ and $X = CH_2CH_2OCH_2CH_2OCH_2CH_2$ and m = 1
11 $R^1 = CH_3$ and $R^2 = CH_3$ and X $CH_2CH_2OCH_2CH_2OCH_2CH_2$ and m = 1
12 $R^1 = CH_3$ and $R^2 = CH_2CH_3$ and $X = CH_2CH_2OCH_2CH_2OCH_2CH_2$ and m = 1
13 $R^1 = H$ and $R^2 = CH_3$ and $X = CH_2CH_2$ and m = 2

FIGURE 8

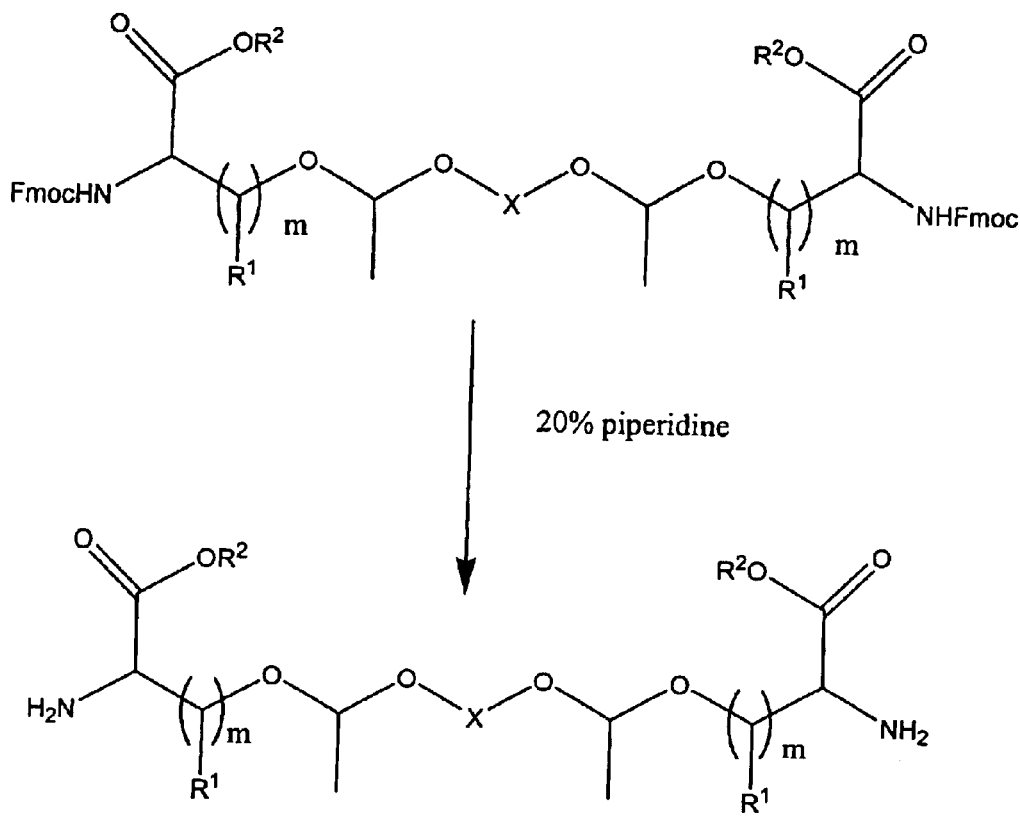

14 $R^1$ = H and $R^2$ = $CH_3$ and X = $CH_2CH_2$ and m = 1

15 $R^1$ = H and $R^2$ = $CH_3$ and X = $CH_2CH_2CH_2CH_2$ and m = 1

16 $R^1$ = H and $R^2$ = $CH_3$ and X = $CH_2CH_2OCH_2CH_2$ and m = 1

17 $R^1$ = H and $R^2$ = $CH_3$ and X = $CH_2CH_2OCH_2CH_2OCH_2CH_2$ and m = 1

18 $R^1$ = H and $R^2$ = $CH_2CH_3$ and X = $CH_2CH_2OCH_2CH_2OCH_2CH_2$ and m = 1

19 $R^1$ = $CH_3$ and $R^2$ = $CH_3$ and X $CH_2CH_2OCH_2CH_2OCH_2CH_2$ and m = 1

20 $R^1$ = $CH_3$ and $R^2$ = $CH_2CH_3$ and X = $CH_2CH_2OCH_2CH_2OCH_2CH_2$ and m = 1

21 $R^1$ = H and $R^2$ = $CH_3$ and X = $CH_2CH_2$ and m = 2

FIGURE 9

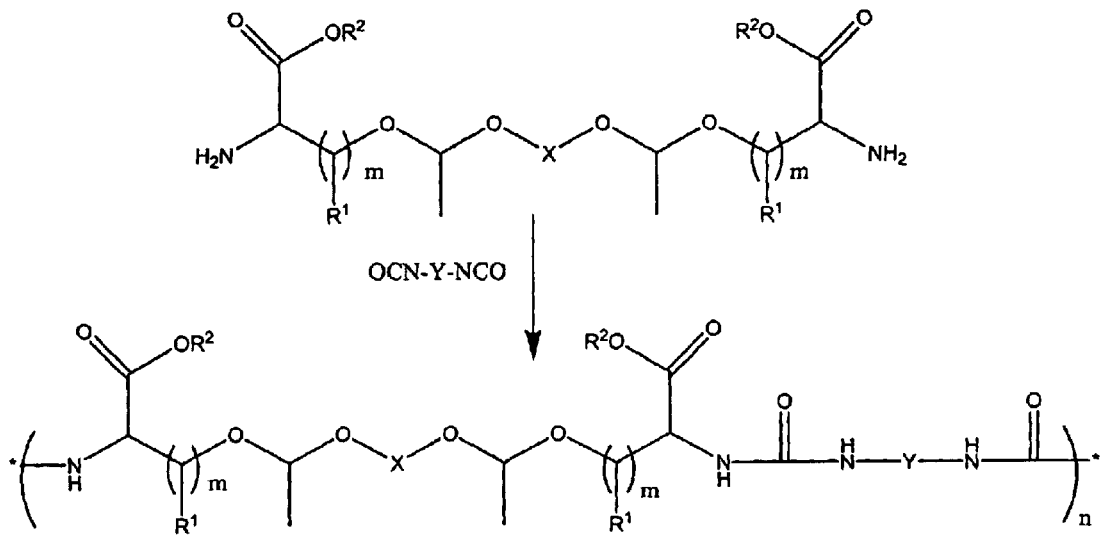

22 $R^1$ = H and $R^2$ = $CH_3$ and X = $CH_2CH_2$ and Y = $C_6H_{12}$ and m =1

23 $R^1$ = H and $R^2$ = $CH_3$ and X = $CH_2CH_2$ and Y = $C_{12}H_{24}$ and m =1

24 $R^1$ = H and $R^2$ = $CH_3$ and X = $CH_2CH_2CH_2CH_2$ and Y = $C_6H_{12}$ and m =1

25 $R^1$ = H and $R^2$ = $CH_3$ and X = $CH_2CH_2CH_2CH_2$ and Y = $C_{12}H_{24}$ and m =1

26 $R^1$ = H and $R^2$ = $CH_3$ and X = $CH_2CH_2OCH_2CH_2$ and Y = $C_6H_{12}$ and m =1

27 $R^1$ = H and $R^2$ = $CH_3$ and X = $CH_2CH_2OCH_2CH_2$ and Y = $C_{12}H_{24}$ and m =1

28 $R^1$ = H and $R^2$ = $CH_3$ and X = $CH_2CH_2OCH_2CH_2OCH_2CH_2$ and Y = $C_6H_{12}$ and m =1

29 $R^1$ = H and $R^2$ = $CH_3$ and X = $CH_2CH_2OCH_2CH_2OCH_2CH_2$ and Y = $C_{12}H_{24}$ and m =1

30 $R^1$ = H and $R^2$ = $CH_2CH_3$ and X = $CH_2CH_2OCH_2CH_2OCH_2CH_2$ and Y = $C_6H_{12}$ and m =1

31 $R^1$ = H and $R^2$ = $CH_2CH_3$ and X = $CH_2CH_2OCH_2CH_2OCH_2CH_2$ and Y = $C_{12}H_{24}$ and m =1

32 $R^1$ = $CH_3$ and $R^2$ = $CH_3$ and X = $CH_2CH_2OCH_2CH_2OCH_2CH_2$ and Y = $C_6H_{12}$ and m =1

33 $R^1$ = $CH_3$ and $R^2$ = $CH_3$ and X = $CH_2CH_2OCH_2CH_2OCH_2CH_2$ and Y = $C_{12}H_{24}$ and m =1

34 $R^1$ = $CH_3$ and $R^2$ = $CH_2CH_3$ and X = $CH_2CH_2OCH_2CH_2OCH_2CH_2$ and Y = $C_6H_{12}$ and m =1

35 $R^1$ = $CH_3$ and $R^2$ = $CH_2CH_3$ and X = $CH_2CH_2OCH_2CH_2OCH_2CH_2$ and Y = $C_{12}H_{24}$ and m =1

36 $R^1$ = H and $R^2$ = $CH_3$ and X = $CH_2CH_2$ and Y = $C_6H_{12}$ and m = 2

37 $R^1$ = H and $R^2$ = $CH_3$ and X = $CH_2CH_2$ and Y = $C_{12}H_{24}$ and m = 2

FIGURE 10

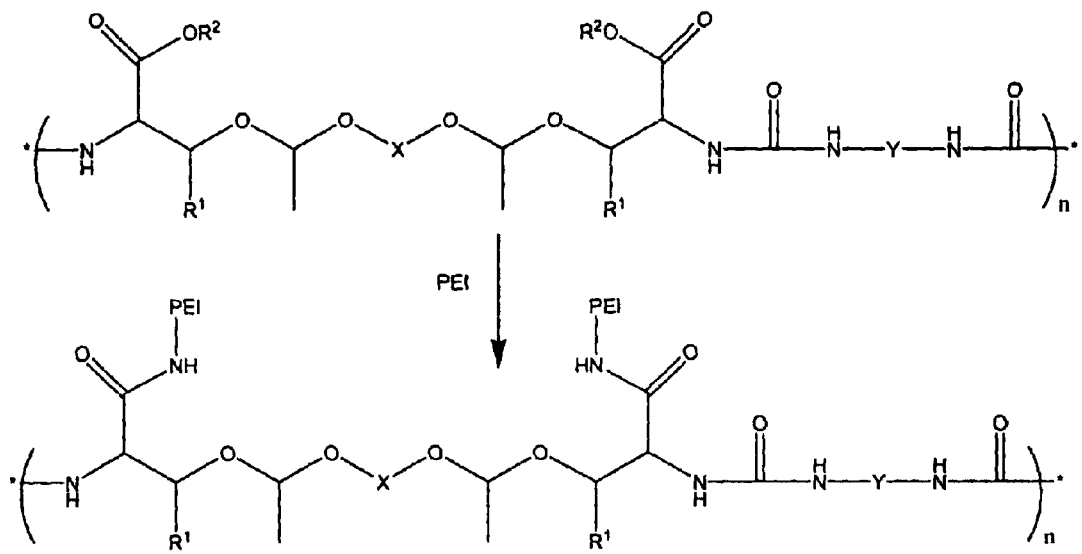

38 $R^1$ = H and $PEI_{600}$ and X = $CH_2CH_2$ and Y = $C_6H_{12}$
39 $R^1$ = H and $PEI_{1800}$ and X = $CH_2CH_2$ and Y = $C_6H_{12}$
40 $R^1$ = H and $PEI_{600}$ and X = $CH_2CH_2$ and Y = $C_{12}H_{24}$
41 $R^1$ = H and $PEI_{1800}$ and X = $CH_2CH_2$ and Y = $C_{12}H_{24}$
42 $R^1$ = H and $PEI_{600}$ and X = $CH_2CH_2CH_2CH_2$ and Y = $C_6H_{12}$
43 $R^1$ = H and $PEI_{1800}$ and X = $CH_2CH_2CH_2CH_2$ and Y = $C_6H_{12}$
44 $R^1$ = H and $PEI_{600}$ and X = $CH_2CH_2CH_2CH_2$ and Y = $C_{12}H_{24}$
45 $R^1$ = H and $PEI_{1800}$ and X = $CH_2CH_2CH_2CH_2$ and Y = $C_{12}H_{24}$
46 $R^1$ = H and $PEI_{600}$ and X = $CH_2CH_2OCH_2CH_2$ and Y = $C_6H_{12}$
47 $R^1$ = H and $PEI_{1800}$ and X = $CH_2CH_2OCH_2CH_2$ and Y = $C_6H_{12}$
48 $R^1$ = H and $PEI_{600}$ and X = $CH_2CH_2OCH_2CH_2$ and Y = $C_{12}H_{24}$
49 $R^1$ = H and $PEI_{1800}$ and X = $CH_2CH_2OCH_2CH_2$ and Y = $C_{12}H_{24}$
50 $R^1$ = H and $PEI_{600}$ and X = $CH_2CH_2OCH_2CH_2OCH_2CH_2$ and Y = $C_6H_{12}$
51 $R^1$ = H and $PEI_{1800}$ and X = $CH_2CH_2OCH_2CH_2OCH_2CH_2$ and Y = $C_6H_{12}$
52 $R^1$ = H and $PEI_{600}$ and X = $CH_2CH_2OCH_2CH_2OCH_2CH_2$ and Y = $C_{12}H_{24}$
53 $R^1$ = H and $PEI_{1800}$ and X = $CH_2CH_2OCH_2CH_2OCH_2CH_2$ and Y = $C_{12}H_{24}$
54 $R^1$ = $CH_3$ and $PEI_{600}$ and X = $CH_2CH_2OCH_2CH_2OCH_2CH_2$ and Y = $C_6H_{12}$
55 $R^1$ = $CH_3$ and $PEI_{1800}$ and X = $CH_2CH_2OCH_2CH_2OCH_2CH_2$ and Y = $C_{12}H_{24}$

ACID-SENSITIVE POLYACETALS AND METHODS

BACKGROUND OF THE INVENTION

1. Field of the Invention

This invention relates generally to biodegradable polymers containing acetal recurring units. More particularly, this invention relates to acid sensitive biodegradable polyacetals, methods for making them, and methods for using them in polynucleotide delivery applications.

2. Description of the Related Art

There is a need for non-viral drug delivery systems having desirable properties such as low immunogenicity, amenable to production on a relatively large scale, and which can be easily modified to provide a range of biological properties. See Mulligan, R. C., "The basic science of gene therapy," Science 260, 926–932 (1993); and Luo, D. & Saltzman, W. M. "Synthetic DNA delivery systems," Nat. Biotechnol. 18, 33–37 (2000). However, non-degradable cationic polymers such as poly(lysine) and polyethyleneimine (PEI) can have significant cytotoxicity. See Choksakulnimitr, S., Masuda, S., Tokuda, H., Takakura, Y. & Hashida, M., "In vitro cytotoxicity of macromolecules in different cell culture systems," J. Control Release 34, 233–241 (1995); Brazeau, G. A., Attia, S., Poxon, S. & Hughes, J. A., "In Vitro Myotoxicity of Selected cationic macrolecules used in non-viral gene therapy," Pharm. Res. 15, 680–684 (1998); and Ahn, C.-H., Chae, S. Y., Bae, Y. H. & Kim, S. W. "Biodegradable poly(ethylenimine) for plasmid DNA delivery," J. Control. Release 80, 273–282 (2002).

To reduce cytotoxicity, some efforts have been made to develop degradable cationic polymers. See Ahn, C.-H., Chae, S. Y., Bae, Y. H. & Kim, S. W., "Biodegradable poly(ethylenimine) for plasmid DNA delivery," J. Control. Release 80, 273–282 (2002); Lynn, D. M. A., D. G.; Putman, D.; Langer, R., "Accelerated Discovery of Synthetic Transfection Vectors: Parallel Synthesis and Screening of a Degradable Polymer Library," J. Am. Chem. Soc. 123 (2001); Lim, Y. et al., "Biodegradable Polyester, Poly[α-(4-Aminobutyl)-1-Glycolic Acid], as a Non-toxic Gene Carrier," Pharmaceutical Research 17, 811–816 (2000); Lim, Y., Kim, S., Suh, H. & Park, J.-S., "Biodegradable, Endosome Disruptive, and Cationic Network-type Polymer as a High Efficient and Non-toxic Gene Delivery Carrier," Bioconjugate Chem. 13, 952–957 (2002); Lim, Y. K., S.; Lee, Y.; Lee, W.; Yang, T.; Lee, M.; Suh, H.; Park, J., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc. 123, 2460–2461 (2001); and Tuominen, J. et al., "Biodegradation of Lactic Acid Based Polymers under Controlled Composting Conditions and Evaluation of the Ecotoxicological Impact," Biomacromolecules 3, 445–455 (2002). However, under physiological conditions, these cationic polymers are susceptible to degradation via base-catalyzed hydrolysis.

Acid-sensitive polymers containing acetal linkages has been reported, see Tomlinson, R. et al., "Pendent Chain Functionalized Polyacetals That Display pH-Dependent Degradation: A Platform for the Development of Novel Polymer Therapeutics," Macromolecules 35, 473–480 (2002); and Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers," J. Am. Chem. Soc. 124, 12398–12399 (2002).

SUMMARY OF THE INVENTION

A preferred embodiment provides a polymer comprising a recurring unit represented by a formula selected from the group consisting of formula (I) and (II):

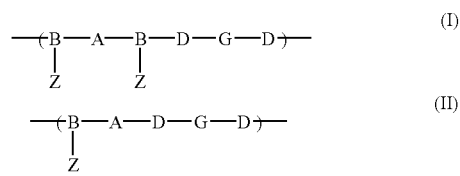

wherein A comprises at least one acetal group;

wherein B is selected from the group consisting of —CH—, —CH(CH$_3$)—, CH$_2$CH—, —CH$_2$C(CH$_3$)—, —CH(CH$_3$)CH— and —CHCH(CH$_3$)CH(CH$_3$)—;

wherein Z is selected from the group consisting of C(O)OR$^1$, C(O)SR$^1$, C(O)NR$^1$R$^2$, and VU;

wherein V is a linker group;

wherein U is selected from the group consisting of poly(ethyleneimine), poly(propyleneimine), poly(lysine), PAMAM dendrimer, octaamine dendrimer, hexadecaamine dendrimer, enhancer, and targeting receptor;

wherein R$^1$ and R$^2$ are each individually selected from the group consisting of hydrogen, C$_1$ to C$_{10}$ alkyl, and C$_6$ to C$_{10}$ aryl;

wherein D is a linkage selected from the group consisting of carboxylic amide, carboxylic ester, urea, and urethane; and wherein G is selected from the group consisting of C$_4$ to C$_{20}$ alkyl, C$_6$–C$_{10}$ aryl, and —(OCH$_2$CH$_2$)$_n$—, where n is in the range of 1 to about 250.

Another preferred embodiment provides a method for making the polymer described above, comprising reacting a monomer represented by a formula selected from the group consisting of formula (III) and formula (IV) with a comonomer having a formula represented by formula (V):

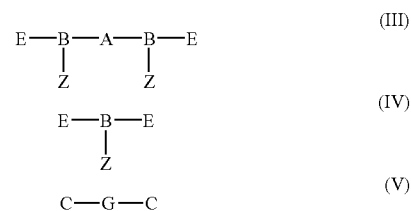

wherein A, B, Z and G have the same meanings as set forth above;

wherein E is selected from the group consisting of —OH, —NH$_2$, and —NH(CH$_3$); and wherein C is selected from the group consisting of isocyanate, NHS-ester, carboxylic acid, carboxylic ester, carboxylic acid chloride and anhydride.

Another preferred embodiment provides a method for making the polymer described above in which V is —C(O)NH—, comprising reacting a compound represented by the formula H$_2$NU with a polymer comprising a recurring unit represented by a formula selected from the group consisting of formula (VII) and (VIII):

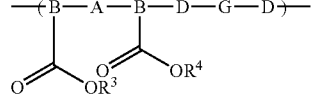
(VII)

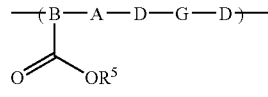
(VIII)

wherein U, A, B, D and G have the same meanings as set forth above; and wherein R$^3$, R$^4$ and R$^5$ are each individually selected from the group consisting of hydrogen, C$_1$ to C$_{10}$ alkyl, and C$_6$ to C$_{10}$ aryl.

Another preferred embodiment provides a complex comprising a polymer as described above and a polynucleotide. Another preferred embodiment provides a method for making such a complex, comprising intermixing the polymer and the polynucleotide. Another preferred embodiment provides a method for transfecting a cell, comprising contacting the cell with such a complex.

Another preferred embodiment provides a polymer as described above in which the recurring unit is represented by a formula selected from the group consisting of formula (IX) and formula (X):

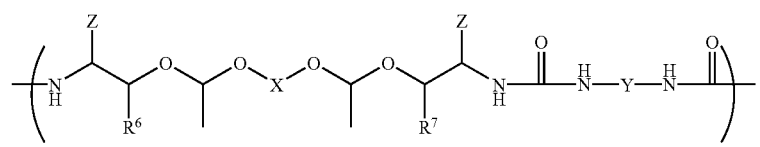
(IX)

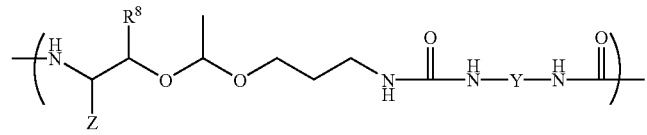
(X)

wherein Z has the same meaning as set forth above; R$^6$, R$^7$ and R$_8$ are each individually selected from the group consisting of H and —CH$_3$; X is selected from the group consisting of —CH$_2$CH$_2$—, —CH$_2$CH$_2$CH$_2$CH$_2$—, —CH$_2$CH$_2$OCH$_2$CH$_2$—, and —CH$_2$CH$_2$OCH$_2$CH$_2$OCH$_2$CH$_2$—; and Y is selected from the group consisting of linear or branched C$_4$H$_8$, C$_5$H$_{10}$, C$_6$H$_{12}$, C$_7$H$_{14}$, C$_8$H$_{16}$, C$_{10}$H$_{20}$, and C$_{12}$H$_{24}$.

Another preferred embodiment provides a method for making a polymer as described above, comprising reacting a monomer represented by a formula selected from the group consisting of formula (XI) and formula (XII) with a comonomer represented by the formula (XIII):

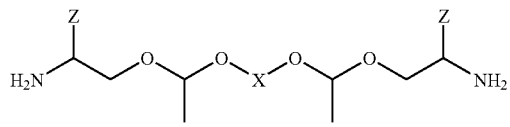
(XI)

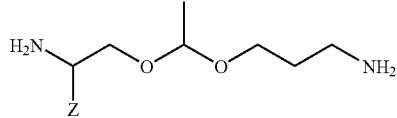
(XII)

$$O=C=N-Y-N=C=O$$ (XIII)

wherein X is selected from the group consisting of CH$_2$CH$_2$, CH$_2$CH$_2$CH$_2$CH$_2$, CH$_2$CH$_2$OCH$_2$CH$_2$, and CH$_2$CH$_2$OCH$_2$CH$_2$OCH$_2$CH$_2$; and wherein Y is selected from the group consisting of linear or branched C$_4$H$_8$, C$_5$H$_{10}$, C$_6$H$_{12}$, C$_7$H$_{14}$, C$_8$H$_{16}$, C$_{10}$H$_{20}$, and C$_{12}$H$_{24}$; and wherein Z is selected from the group consisting of C(O)OR$^1$, C(O)SR$^1$, and C(O)NR$^1$R$^2$, where R$^1$ and R$^2$ are each individually selected from the group consisting of hydrogen, C$_1$ to C$_{20}$ alkyl, and C$_6$–C$_{10}$ aryl.

Another preferred embodiment provides a method for making a polymer as described above, comprising reacting a poly(ethyleneimine) with a polymer comprising a recurring unit represented by a formula selected from the group consisting of formula (XIV) and formula (XV):

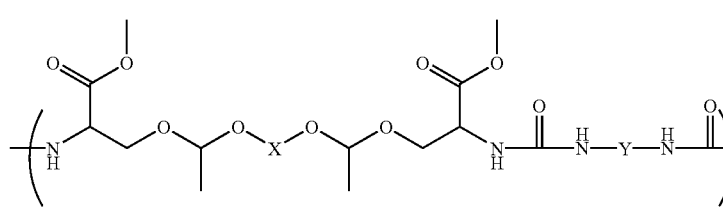

(XIV)

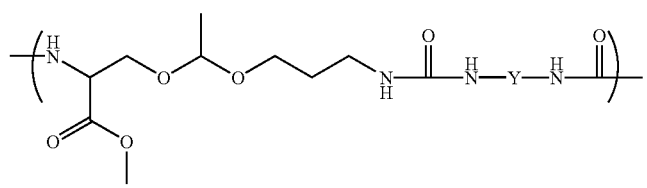

(XV)

where X is selected from the group consisting of $CH_2CH_2$, $CH_2CH_2CH_2CH_2$, $CH_2CH_2OCH_2CH_2$, and $CH_2CH_2OCH_2CH_2OCH_2CH_2$; and Y is selected from the group consisting of linear or branched $C_4H_8$, $C_5H_{10}$, $C_6H_{12}$, $C_7H_{14}$, $C_8H_{16}$, $C_{10}H_{20}$, and $C_{12}H_{24}$.

Another preferred embodiment provides a monomer represented by a formula selected from the group consisting of formula (XI) and formula (XII):

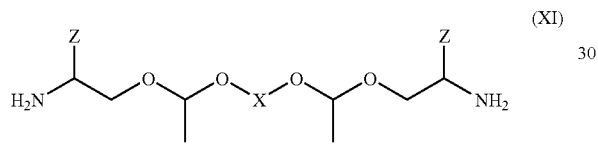

(XI)

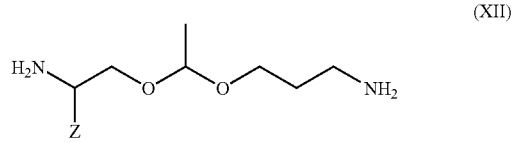

(XII)

where X is selected from the group consisting of $-CH_2CH_2-$, $-CH_2CH_2CH_2CH_2-$, $-CH_2CH_2OCH_2CH_2-$, and $-CH_2CH_2OCH_2CH_2OCH_2CH_2-$; Z is selected from the group consisting of $C(O)OR^1$, $C(O)SR^1$, and $C(O)NR^1R^2$, and $R^1$ and $R^2$ are each individually selected from the group consisting of hydrogen, $C_1$ to $C_{20}$ alkyl, and $C_6$–$C_{10}$ aryl.

Another preferred embodiment provides a method for making such a monomer, comprising reacting a divinyl ether represented by formula (XVI) with about two equivalents of an ester represented by formula (XVII), in the presence of an acid in a non-alcoholic organic solvent:

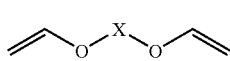

(XVI)

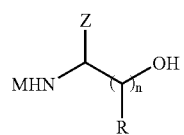

(XVII)

wherein X is selected from the group consisting of $-CH_2CH_2-$, $-CH_2CH_2CH_2CH_2-$, $-CH_2CH_2OCH_2CH_2-$, and $-CH_2CH_2OCH_2CH_2OCH_2CH_2-$;

wherein Z is selected from the group consisting of $C(O)OR^1$, $C(O)SR^1$, and $C(O)NR^1R^2$, where $R^1$ and $R^2$ are each individually selected from the group consisting of hydrogen, $C_1$ to $C_{20}$ alkyl, and $C_6$–$C_{10}$ aryl;

wherein M is a protecting group selected from the group consisting of 9-fluorenylmethyl carbamate, activated amide, and cyclic imide; and wherein n is 1 or 2.

These and other embodiments are described in greater detail below.

BRIEF DESCRIPTION OF THE DRAWINGS

FIG. 4 shows reproductions of photographs of Green Fluorescent Protein (GFP) signals using polyacetals 46–51, Lipofectamine 2000 (L2000, positive control), and poly(ethylenimine)-1800 (PEI-1800, negative control). The results show that the polyacetals have a high transfection efficiency than PEI-1800.

(L2000) in the cytotoxicity assay. The results show that polyacetals do not display cytotoxicity in this assay. Labeling: Ratio of polymer:DNA (by weight) for vertical line bar is 32:1, horizontal line bar is 16:1, and downward diagonal line bar is 8:1.

Figure 6:
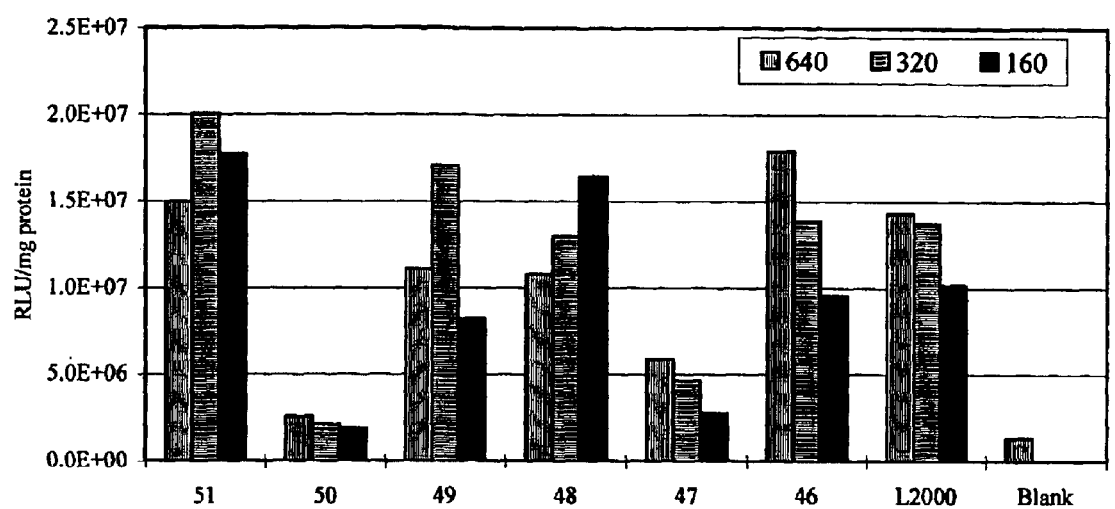

FIG. 6 shows a bar graph plotting Relative Light Units (RLU) per milligram of protein for transfection of Luc 705 cells with antisense DNA oligo using polyacetals 46–51, a commercial transfection reagent L2000 (Lipofectamine 2000, positive control), and a blank (negative control). The results show that the transfection of the polyacetals is better than the best commercially available transfection agent currently known, Lipofectamine 2000. Labeling: Ratio of polymer:DNA (by weight) for vertical line bar is 640:1, horizontal line bar is 32:1, downward diagonal line bar is 16:1.

FIG. 7 shows a preferred reaction scheme for the synthesis of protected monomers 6–13.

FIG. 8 shows a preferred reaction scheme for the preparation of monomers 14–21.

FIG. 9 shows a preferred reaction scheme for the preparation of polyacetals 22–37.

FIG. 10 shows a preferred reaction scheme for the preparation of polyacetals 38–55.

Figure 11:
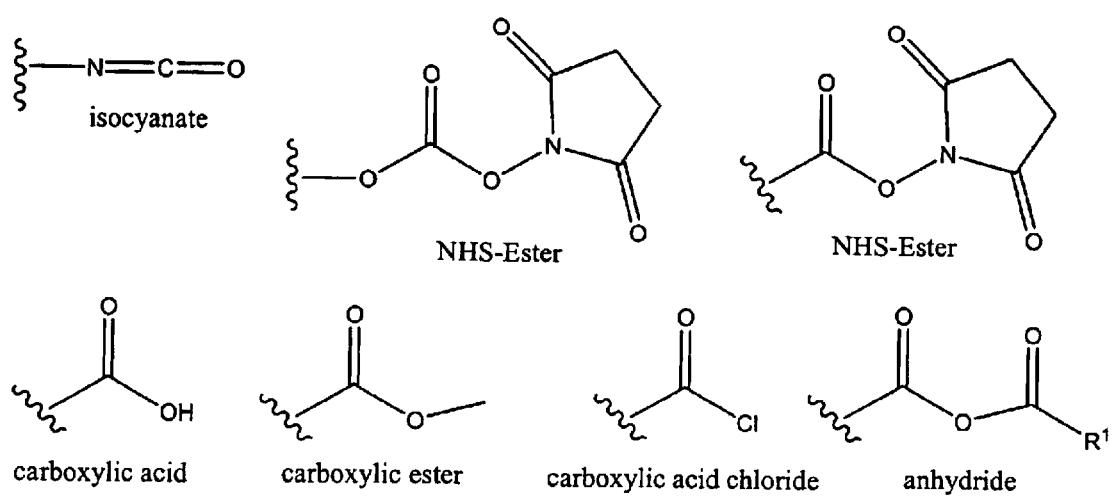

FIG. 11 shows the chemical structures for various reactive end groups represented by C in formula (V).

DETAILED DESCRIPTION OF THE PREFERRED EMBODIMENTS

Preferred embodiments are directed to polyacetals, methods of making polyacetals, monomers useful for making polyacetals, complexes comprising polyacetals and polynucleotides, methods of making such complexes, and methods of transfecting cells using such complexes.

Polyacetals are polymers that contain acetal (—O—CHR—O—) recurring units. Preferably, R is methyl. Preferred polyacetals comprise a recurring units represented by a formula selected from the group consisting of formula (I) and (II):

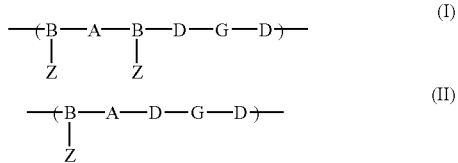

In formulae (I) and (II), A represents a linker group that comprises at least one acetal group; B is selected from the group consisting of —CH—, —CH(CH$_3$)—, CH$_2$CH—, —CH$_2$C(CH$_3$)—, —CH(CH$_3$)CH—, and —CHCH(CH$_3$)CH(CH$_3$)—; Z is selected from the group consisting of C(O)OR$^1$, C(O)SR$^1$, C(O)NR$^1$R$^2$, and VU; V is a linker group; U is selected from the group consisting of poly(ethyleneimine), poly(propyleneimine), poly(lysine), PAMAM dendrimer, octaamine dendrimer, hexadecaamine dendrimer, enhancer, and targeting receptor; R, R$^1$ and R$^2$ are each individually selected from the group consisting of hydrogen, C$_1$ to C$_{10}$ alkyl, and C$_6$ to C$_{10}$ aryl; D is a linkage selected from the group consisting of carboxylic amide, carboxylic ester, urea, and urethane; and G is selected from the group consisting of C$_4$ to C$_{20}$ alky, C$_6$–C$_{10}$ aryl, and —(OCH$_2$CH$_2$)$_n$—, where n is in the range of 1 to about 250. In this context, a "linker group" is a bifunctional chemical group that joins one chemical group to another. Linker groups can contain a single bifunctional chemical group such as amide, or may contain two chemical groups such as amide-amide, amide-alkyl, alkyl-amide, amine-amide, or thioether-amide. Examples of preferred linker groups include —C(O)NH—, —C(O)NH—R$^9$—C(O)NH—, —C(O)NH—R$^9$—, —R$^9$—C(O)NH—, —NH—R$^9$—C(O)NH—, —S—R$^9$—C(O)NH, where R$^9$ is selected from the group consisting of hydrogen, C$_1$ to C$_{10}$ alkyl, and C$_6$ to C$_{10}$ aryl. Examples of linker groups that comprise at least one acetal group include —OCH(CH$_3$)O—, —OCH(CH$_3$)OCH(CH$_3$)O—, —OCH(CH$_3$)O—CH$_2$CH$_2$—OCH(CH$_3$)O—, —OCH(CH$_3$)O—CH$_2$CH$_2$CH$_2$CH$_2$—OCH(CH$_3$)O—, —OCH(CH$_3$)O—CH$_2$CH$_2$OCH$_2$CH$_2$—OCH(CH$_3$)O—, and —OCH(CH$_3$)O—CH$_2$CH$_2$OCH$_2$CH$_2$OCH$_2$CH$_2$—OCH(CH$_3$)O—.

In formulae (I) and (II), Z is selected from the group consisting of C(O)OR$^1$, C(O)SR$^1$, C(O)NR$^1$R$^2$, and VU; V is a linker group; U is selected from the group consisting of poly(ethyleneimine) (PEI), poly(propyleneimine) (PPI), poly(lysine), PAMAM dendrimer, octaamine dendrimer, hexadecaamine dendrimer, enhancer, and targeting receptor. PEI and PPI, if used, preferably have a molecular weight in the range of about 200 to about 100,000 Daltons. Poly(lysine), if used, preferably has a molecular weight in the range of about 200 to about 50,000 Daltons. Molecular weights of polymers referred to herein are weight average molecular weights as measured by high performance size exclusion chromatography (light scattering detector).

In this context, an "enhancer" is a functional group that is capable of enhancing the efficiency of gene transfection to a eukaryotic cell and a "targeting receptor" is a functional group that is capable of recognizing specific receptors on a cell surface. The foregoing definitions are not mutually exclusive, and thus U may be both an enhancer and a targeting receptor. Preferably, U is selected from the group consisting of lipid, cholesterol, transferrin, antibody, antibody fragment, galactose, mannose, lipoprotein, lysosomotrophic agent, and fusogenic agent. Enhancers and targeting receptors may be attached to polyacetals in various ways, e.g., by covalent bonding to the polyacetal via a linker group V, or by conjugating an enhancer and/or a targeting receptor to Z, or both. Thus, two or more enhancers and/or targeting receptors may be attached to a polyacetal.

Polyacetals may be copolymers and thus may contain two or more different recurring units represented by the formulas (I) and/or (II), and/or other recurring units. Terms such as "polyacetal of the formula (I)", "polyacetal of the formula (II)", "polymer of the formula (I)", and "polymer of the formula (II)" thus include copolymers as well as homopolymers consisting essentially of recurring units of the formula (I) or (II).

Various methods may be used to make polyacetals. A preferred method comprises reacting a monomer represented by a formula selected from the group consisting of formula (III) and formula (IV) with a comonomer having a formula represented by formula (V):

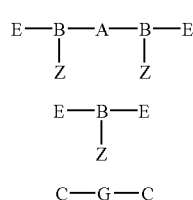

(III)

(IV)

(V)

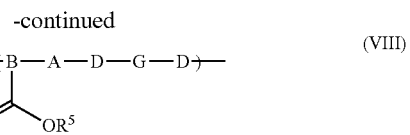

(VIII)

In formulae (III), (IV) and (V), A, B, Z and G have the same meanings as set forth above, E is a reactive end group preferably selected from the group consisting of —OH, —NH$_2$, and —NH(CH$_3$); and C is a reactive end group preferably selected from the group consisting of isocyanate, NHS-ester, carboxylic acid, carboxylic ester, carboxylic acid chloride and anhydride. FIG. 11 illustrates chemical structures for various reactive end groups represented by C in formula (V). The polymerization reaction conditions are adjusted in a manner generally known to those skilled in the art, depending on the nature of the reactive end groups E and C. See G. Odian, Principles of Polymerization 3$^{rd}$ Ed. (1991). Optionally, the polymerization may be conducted in the presence of one or more additional comonomers having compatible reactive end groups. Preferably, the mole ratio of monomers (III) and/or (IV) to comonomer (V) in the mixture is approximately 1:1, although the exact ratio may be varied to adjust the molecular weight of the resulting polymer and/or to compensate for the presence of additional comonomers. Higher molecular weights are generally achieved when the ratio is closer to 1:1. Lower molecular weights may be achieved by using a slight excess of either the monomers (III)/(IV) or comonomer (V), and/or by including small amounts of monofunctional reactants. Preferably, the molecular weights of the resulting polyacetals (e.g., a polymer or copolymer comprising a recurring unit represented by the formulae (I) and/or (II)) are about 1,000 Daltons or greater, more preferably in the range of about 1,000 to about 250,000 Daltons.

Recurring units represented by the formulae (I) and (II) encompass two genera, one in which Z is selected from the group consisting of C(O)OR$^1$, C(O)SR$^1$, and C(O)NR$^1$R$^2$, and the other in which Z is VU. Polyacetals in which Z is selected from the group consisting of C(O)OR$^1$, C(O)SR$^1$, and C(O)NR$^1$R$^2$ are useful for making polyacetals in which Z is VU. For example, polyacetals comprising a recurring unit of the formula (I) in which Z is VU and V is —C(O)NH— are preferably made by reacting a compound represented by the formula H$_2$NU with a polyacetal comprising a recurring unit of the formula (I) in which Z is C(O)OR$^1$, as shown in formulae (VII) and (VIII):

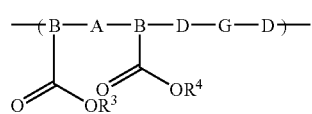

(VII)

In formulae (VII) and (VIII), U, A, B, D and G have the same meanings as set forth above, and R$^3$, R$^4$ and R$^5$ are each individually selected from the group consisting of hydrogen, C$_1$ to C$_{10}$ alkyl, and C$_6$ to C$_{10}$ aryl. For the compound represented by the formula H$_2$NU, U has the same meaning as set forth above. The reaction of the compound represented by the formula H$_2$NU with the polyacetal of the formula (VII) or (VIII) is preferably conducted in a polar solvent such as dimethylformamide. The polyacetals of the formulae (VII) and (VIII) may be prepared by reacting corresponding monomers of the formulae (III), (IV) and (V) as described above. A "polyacetal of the formula (VII)", "polyacetal of the formula (VIII)", "polymer of the formula (VII)", or "polymer of the formula (VIII)", as those terms are used herein, includes copolymers comprising a recurring unit of the formula (VII) and/or (VIII) as well as homopolymers consisting essentially of recurring units of the formula (VII) or (VIII).

Figure 1:
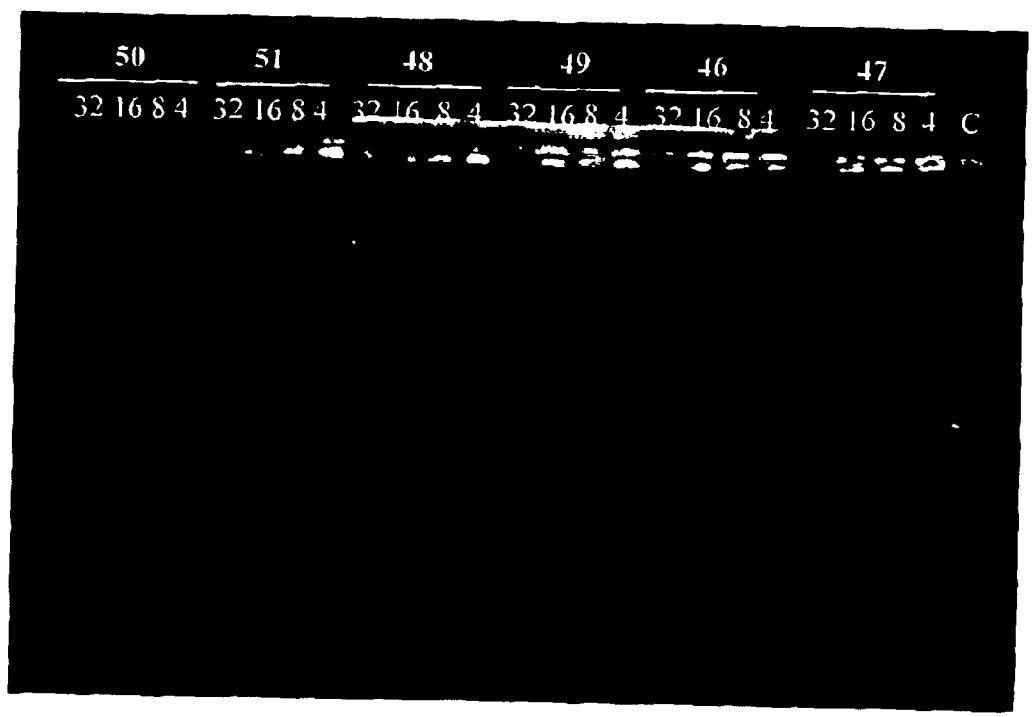
FIG. 1 shows a reproduction of a photograph of a nucleotide retardation assay using degradable polymers and a control (C). The assay shows that polyacetals 46–51 formed complexes with polynucleotides at various ratios of polymer to polynucleotide (32:1, 16:1, 8:1, 4:1, by weight/weight), as compared to a control (C) (no polymers).

It has been found that polyacetals of the formulae (I) and (II) in which Z is VU form complexes with polynucleotides such as DNA (e.g., plasmid DNA, antisense DNA and DNA oligomers) and RNA (e.g., siRNA). Thus, another embodiment provides a complex comprising a polyacetal of the formula (I) or (II) and a polynucleotide, in which the Z in the polyacetal of the formula (I) or (II) is VU, where Z, V and U have the same meanings as set forth above. Preferably, V is —C(O)NH—. Such complexes are preferably formed by intermixing the polyacetal of the formula (I) or (II) (in which Z is VU) and a polynucleotide. Preferably, such intermixing is conducted by adding a solution containing the polyacetal to a second solution containing the polynucleotide. Complexation may be verified by examining the retardation of the polynucleotide-polyacetal band on agarose gel electrophoresis, as shown in FIG. 1.

Figure 2:
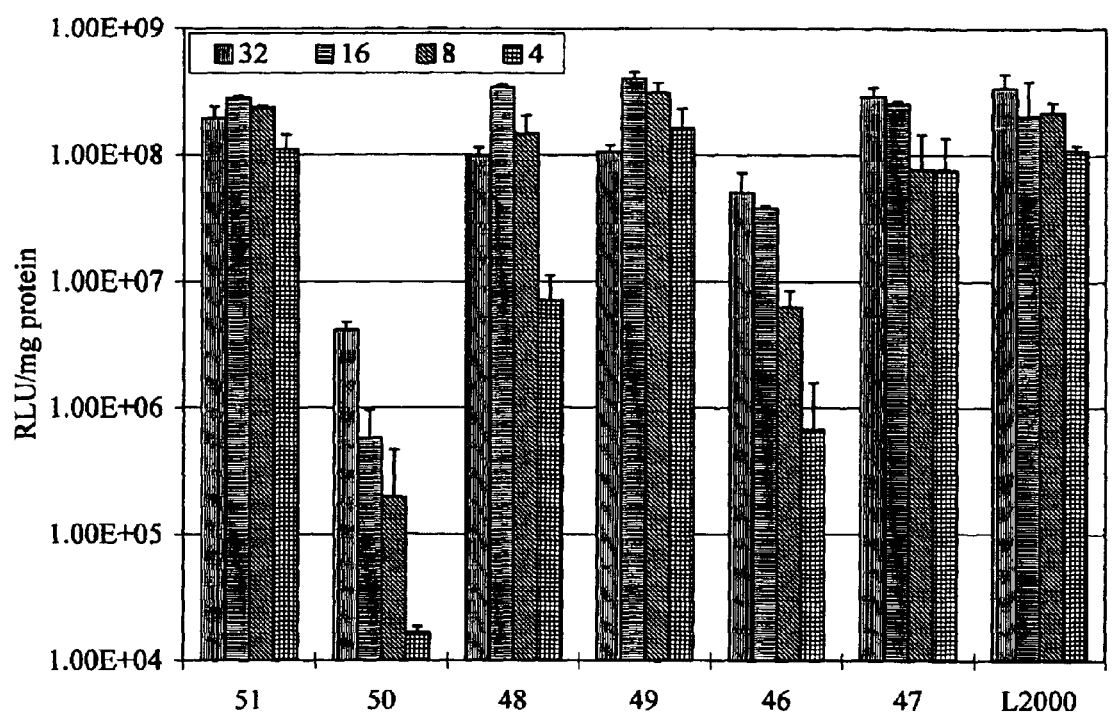
FIG. 2 shows a bar graph plotting Relative Light Units (RLU) per milligram of protein for transfection of 293 human kidney embryonic cells with plasmid DNA using degradable polymers 46–51 and a commercial transfection reagent L2000 (Lipofectamine 2000, positive control). The results show that the transfection of the polyacetals is comparable to the best commercially available transfection agent currently known, Lipofectamine 2000. Labeling: Ratio of polymer:DNA (by weight) for vertical line bar is 32:1, horizontal line bar is 16:1, downward diagonal line bar is 8:1, and grid line bar is 4:1.
Figure 3:
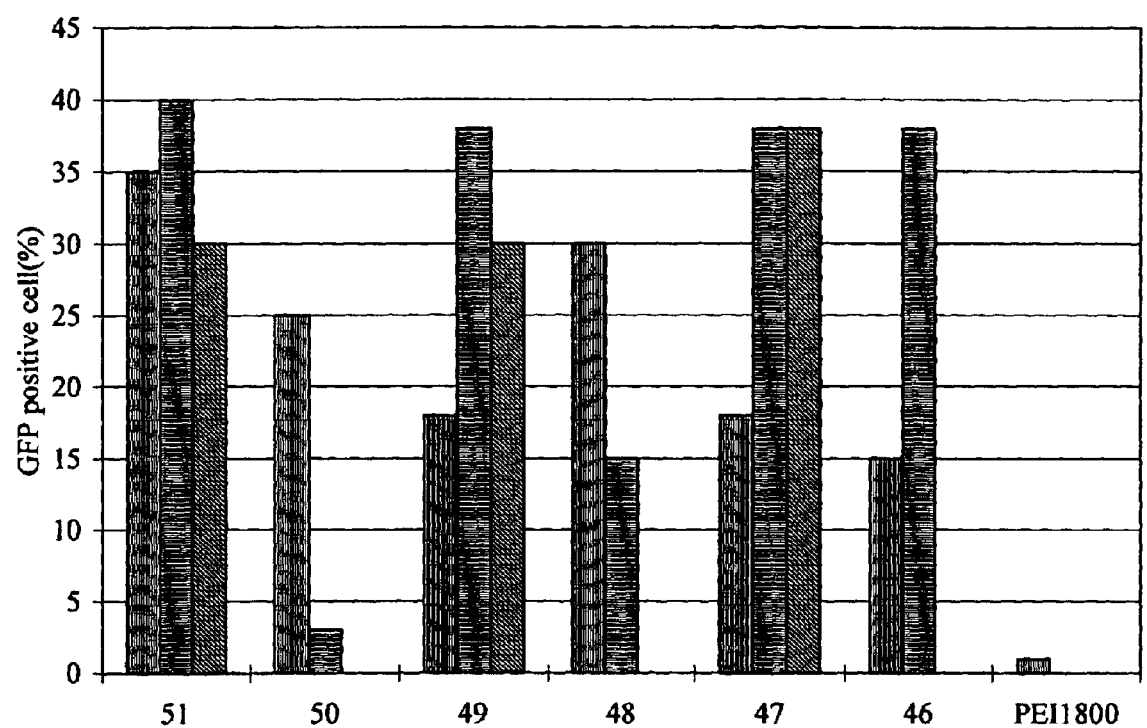
FIG. 3 shows a bar graph plotting GFP transfection signal (%) of 293 human kidney embryonic cells with plasmid DNA using polyacetals 46–51 and a commercial agent poly(polyethylenimine)-1800 (PEI-1800, negative control). The results show that polymers 46–51 have a higher transfection efficiency than poly(ethylenimine)-1800. Labeling: Ratio of polymer:DNA (by weight) for vertical line bar is 32:1, horizontal line bar is 16:1, and downward diagonal line bar is 8:1.

It has been found that complexes comprising polyacetals of the formulae (I) or (II) (in which Z is VU) and polynucleotides are useful for transfecting cells. Transfection is preferably conducted by contacting the cell with the complex. The examples below illustrate the use of polyacetal-DNA complexes for the transfection of human embryonic kidney cells ("293 cells"), as shown in FIGS. 2 and 3. It has been found that preferred complexes comprising polymers of the formulae (I) and (II) (in which Z is VU) and polynucleotides are relatively non-toxic. The examples below illustrate the cytotoxicity of polyacetal-DNA complexes on mammalian cells as evaluated using a 3-[4,5 dimethylthiazol-2-yl]-2,5-diphenyltetrazolium bromide (MTT) method (see FIG. 5).

Thus, a preferred embodiment provides a method for transfecting a cell, comprising contacting the cell with a polyacetal of the formulae (I) or (II) (in which Z is VU) and a polynucleotide. Preferably, V is —C(O)NH—; also preferably, U is poly(ethyleneimine). Examples of preferred polyacetals include those comprising a recurring unit that is represented by a formula selected from the group consisting of formula (IX) and formula (X):

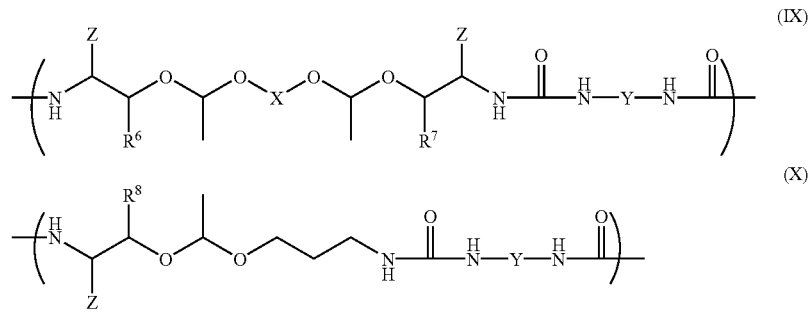

(IX)

(X)

In formulae (IX) and (X), Z has the same meaning as described above; $R^6$, $R^7$ and $R_8$ are each individually selected from the group consisting of H and —$CH_3$; X is selected from the group consisting of —$CH_2CH_2$—, —$CH_2CH_2CH_2CH_2$—, —$CH_2CH_2OCH_2CH_2$—, and —$CH_2CH_2OCH_2CH_2OCH_2CH_2$—; and Y is selected from the group consisting of linear or branched $C_4H_8$, $C_5H_{10}$, $C_6H_{12}$, $C_7H_{14}$, $C_8H_{16}$, $C_{10}H_{20}$, and $C_{12}H_{24}$. Z is preferably VU, V is preferably C(O)NH—, and U is preferably poly(ethyleneimine), poly(lysine), an enhancer, or a targeting receptor. The poly(ethylenimine) preferably has a molecular weight in the range of about 200 to about 100,000 Daltons; the poly(lysine) preferably has a molecular weight in the range of about 200 to about 50,000 Daltons. Non-limiting examples of preferred enhancers include those selected from the group consisting of lipid, cholesterol, lipoprotein, fatty acid, lysosomotrophic agent, and fusogenic agent. Non-limiting examples of preferred targeting receptors include those selected from the group consisting of transferrin, antibody, antibody fragment, galactose, and mannose.

Polyacetals comprising recurring units of the formulae (IX) and (X) may be prepared in the same general manner as described above for the preparation of polyacetals comprising recurring units of the formulae (I) and (II) as described above. For example, a preferred embodiment provides a method comprising reacting a monomer represented by a formula selected from the group consisting of formula (XI) and formula (XII) with a comonomer represented by the formula (XIII), in which X, Y and Z have the same meanings as for the recurring units of the formulae (IX) and (X) described above:

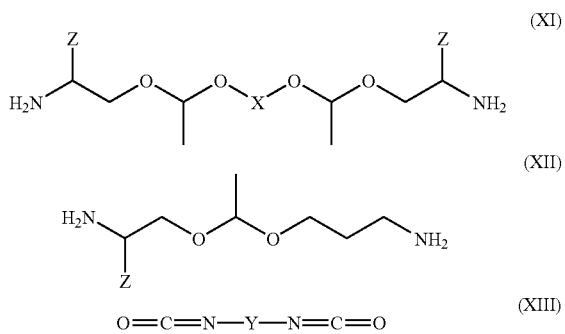

(XI)

(XII)

(XIII)

Polyacetals comprising recurring units of the formulae (IX) and (X) may also be prepared by reacting a compound of the formula $H_2NU$ with a polymer comprising a recurring unit represented by a formula selected from the group consisting of formula (XIV) and formula (XV), in which X and Y have the same meanings as for the recurring units of the formulae (IX) and (X) described above:

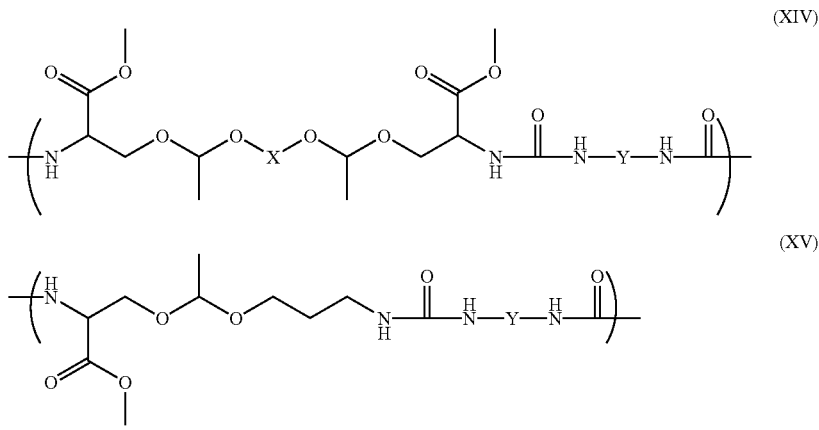

(XIV)

(XV)

Another preferred embodiment provides a monomer represented by the formula (XI). A preferred method for making such monomers comprises reacting a divinyl ether represented by formula (XVI) with about two equivalents of a compound represented by formula (XVII), in the presence of an acid in a non-alcoholic organic solvent:

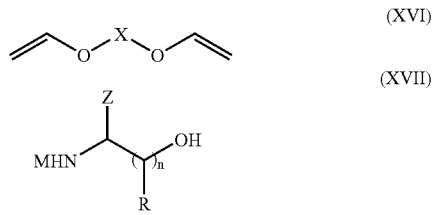

In formulae (XVI) and (XVII), X is selected from the group consisting of —$CH_2CH_2$—, —$CH_2CH_2CH_2CH_2$—, —$CH_2CH_2OCH_2CH_2$—, and —$CH_2CH_2OCH_2CH_2OCH_2CH_2$—; Z is selected from the group consisting of $C(O)OR^1$, $C(O)SR^1$, and $C(O)NR^1R^2$; $R^1$ and $R^2$ are each individually selected from the group consisting of hydrogen, $C_1$ to $C_{20}$ alkyl, and $C_6$–$C_{10}$ aryl; M is a protecting group selected from the group consisting of 9-fluorenylmethyl carbamate, activated amide, and cyclic imide; R is methyl or hydrogen; and n is 1 or 2.

EXAMPLES

Cell lines and cultures used in the following examples were prepared as follows: Human embryonic kidney cells ("293 cells") were grown in Dulbecco's-modified Eagle's medium (DMEM) containing 10% (v/v) heat-inactivated fetal bovine serum (FBS), 100 U/ml Penicillin and 100 μg/ml streptomycin, and incubated at 37° C. at 100% humidity atmosphere containing 7.5% $CO_2$.

GFP plasmids used in the following examples were prepared as follows: Plasmid pCMV-GFP was purchased from Clontech (Palo Alto, Calif.). The expression of green fluorescent protein (GFP) cDNA is controlled by human cytomegalovirus (CMV) promoter and the transcripts are stabilized by a gene expression enhancer, chicken β-globulin intron. The plasmid vector pCMV-luc was constructed by cloning the firefly luciferase gene into pCMV-0, with the same backbone of mammalian expression vector. The plasmid was expanded in DH5α E. coli and purified with a Plasmid Maxi Kit (obtained commercially from Qiagen, Valencia, Calif.) according to the manufacturer's instructions. The quantity and quality of the purified plasmid DNA was assessed by spectrophotometric analysis at 260 and 280 nm as well as by electrophoresis in 0.8% agarose gel. Purified plasmid DNA was resuspended in sterile distilled, deionized $H_2O$ and frozen.

All the chemicals and reagents for preparing the polyacetals were purchased from Aldrich Chemical Company. Starting materials 1 and 2 (FIG. 7) were prepared by reacting serine methyl ester hydrochloride and serine ethyl ester hydrochloride, respectively, with 9-fluorenylmethyl chloroformate (Fmoc-Cl) as described in the literature (see Carpino, L. A.; Han, G. Y.; J. Org. Chem. 1972, 37, 3404–3409). Starting materials 3, 4, and 5 were prepared by reacting threonine, threonine, and homoserine, respectively, with Fmoc-Cl as described in the literature, followed by stirring in thionyl chloride in methanol, ethanol, and methanol, respectively.

EXAMPLES 1–8

Protected monomers 6–13 were prepared according to the reaction scheme shown in FIG. 7. The following description for the synthesis of protected monomer 7 is illustrative: Di(ethylene glycol) divinyl ether (1.62 g, 10.3 mmol) and protected serine methyl ester 1 (7.00 g, 20.5 mmol) were stirred in tetrahydrofuran (THF) in the presence of molecular sieves (5.00 g) at room temperature for 20 min. A catalytic amount of toluenesulfonic acid (TSA, 0.20 g, 1.0 mmol) was added into the mixture and stirring was continued for 1 day. The reaction mixture was quenched with saturated sodium carbonate in water (30 mL). The organic phase was extracted with ethyl acetate (2×50 mL). The extracts were combined, dried with sodium sulfate, filtered, and concentrated by rotary evaporation. The residue was placed under high vacuum to give protected monomer 7 (8.0 g, 9.51 mmol, 97%) as an oil.

EXAMPLES 9–16

Monomers 14–21 were prepared by de-protection of protected monomers 6–13, respectively, according to the reaction scheme shown in FIG. 8. The following description for the synthesis of monomer 16 is illustrative: A solution (5 mL) of 20% piperidine in THF was added into protected monomer 8 (1.0 g, 1.2 mmol). The mixture was stirred for 2 hours. The reaction mixture was added with hexane (15 mL) and oily precipitate formed. The oily residue was obtained by decanting the solution and redissolved with dichloromethane (DCM, 5 mL) and stirred for 5 hours. Water (5 mL) was added into the mixture and the organic phase was extracted with DCM (2×10 mL). The extracts were combined, dried with sodium sulfate, filtered, and concentrated by rotary evaporation. The residue was placed under high vacuum to give monomer 16 (0.30 g, 0.75 mmol, 63%) as an oil.

EXAMPLES 17–32

Polyacetals 22–37 were prepared by copolymerizing monomers 14–21 with various diisocyanate comonomers according to the reaction scheme shown in FIG. 9. The following description for the preparation of polyacetal 26 is illustrative: A solution of OCN—$C_6H_{12}$—NCO in THF (2 mL) (0.049 g, 0.40 mmol) was added into monomer 16 (0.12 g, 0.29 mmol). The mixture was stirred for 15 min and the reaction mixture was solidified. THF (3 mL) was added into the reaction mixture and sonicated for 5 min. The residue was filtered and washed with THF and diethyl ether. The residue was placed under high vacuum to give polyacetal 26 (0.10 g, 0.19 mmol, 67%) as a white solid.

EXAMPLES 33–50

Polyacetals 38–55 were prepared by reacting polyacetals 22–37 with poly(ethyleneimine) (PEI) according to the reaction scheme shown in FIG. 10. The following description for the preparation of polyacetal 47 is illustrative: A solution of $PEI_{1800}$ (1.3 g) in DMF (1.7 g) was added into polyacetal 26 (0.025 g) and stirred for 3 days at room temperature. THF (25 mL) was added into the reaction mixture and continued to stir for 14 hours and an oily precipitate formed. The residue was obtained by decanting the solution and washed with more THF and diethylether. The residue was placed under high vacuum to give polyacetal 47 (0.20 g) as an oil.

EXAMPLE 51

Retardation of polynucleotide-polymer complexes: Various amounts of polyacetals 46–51 (ratios of polyacetal to polynucleotide of 32:1, 16:1, 8:1, 4:1, by weight/weight) in 10 µl DMEM (without serum and antibiotic) were added dropwise into 0.2 µg GFP plasmid in 10 µl DMEM (without serum and antibiotic) with vortexing. The resulting complexes were placed at room temperature for 15 min prior to electrophoresis. Five µl of loading dye was added to each sample, and 15 µl of each sample were loaded per well in a 0.3% agarose gel. The complexes were analyzed by electrophoresis with 0.04 M Tris-acetate buffer, pH 7.4, containing 1 mM EDTA, at 100 V for 30 minutes. The complexes were visualized by UV illumination. The polynucleotide (plasmid DNA) complexed to the degradable polymer was retarded in the agarose gel, so that greater retardation indicated greater binding between the polymer and the polynucleotide as compared to control C (without polyacetal), as shown in FIG. 1.

EXAMPLE 52

In vitro transfection using polyacetals 46–51 was carried out as follows: Permanent 293 human embryonic kidney cells (adhesive common cells) and K562 human hematopoietic cells (suspension specialized cells) were plated in 24-well tissue culture plates ($2 \times 10^5$ cells/well) and incubated overnight in DMEM with 10% fetal bovine serum (FBS). For each well, a 30 µl aliquot of polyacetal solution (each containing a different dose of polyacetal, ratios of polyacetal to polynucleotide of 32:1, 16:1, 8:1, 4:1, by weight/weight) was added dropwise into a 30-µl DNA solution containing 0.6 µg of plasmid DNA, e.g. pCMV-GFP plasmid DNA or pCMV-luc, while vortexing. Dropwise addition while vortexing was found to be highly preferable, because it was found that transfection results depended on the mixing conditions. The mixed DNA and polyacetal solutions were incubated for 15 min at room temperature to form DNA-polyacetal complexes. Then 60 uL of DNA-polyacetal complex was added into each well and the cells were incubated (37° C., 7.5% $CO_2$) for 24 hours. After that incubation, fruitfly luciferase activities and GFP signals were detected as described below. Commercial transfection reagent Lipofectamine 2000 (L2000) was used as a positive control according to the protocol provided by manufacturer and commercial transfection reagent polyethylenimine-1800 daltons ($PEI_{1800}$) was used as a negative control.

EXAMPLE 53

Transfection results for DNA-polyacetal complexes made using polyacetals 46–51: Luciferase activity was measured using a chemiluminescent assay following the manufacturer's instructions (Luciferase Assay System; Promega, Madison, Wis., USA). About twenty four hours after the transfections described in Example 52 above, the cells were rinsed twice with PBS and then were lysed with lysis buffer (1% Triton X-100, 100 mM $K_3PO_4$, 2 mM dithiothreitol, 10% glycerol, and 2 mM EDTA pH 7.8) for 15 min at room temperature. A 10-µl aliquot of cell lysate was then mixed with 50-µl of luciferase assay reagent with injector at room temperature in the luminometer. Light emission was measured over 10 seconds and expressed as RLUs (relative light units). Relative light units (RLU) were normalized to the protein content of each sample, determined by BSA protein assay (Pierce, Rockford, Ill.). All the experiments were conducted in triplicate. The results obtained for the transfection of 293 cells with pCMV-luc using degradable polymers and L2000 (positive control) are shown in FIG. 2. These results show that transfection efficiencies of polymers are at the same level of the current best commercial agent Lipofectamine 2000.

EXAMPLE 54

GFP observations under fluorescent microscope: Green fluorescent signal in cells were observed under fluorescent microscope (Olympus, filter 520 nm). Cells were photographed using a 10× objective. The percent of cells with GFP signal in transfected cultures was determined from counts of three fields for optimal cationic polymer amounts. The results obtained for the transfection of 293 cells with pCMV-GFP using degradable polyacetals and PEI-1800 (negative control) are shown in FIG. 3. These results show that transfection efficiencies of polymers are much better compared with commercial agent poly(ethylenimine)-1800 daltons.

EXAMPLE 55

Figure 5:
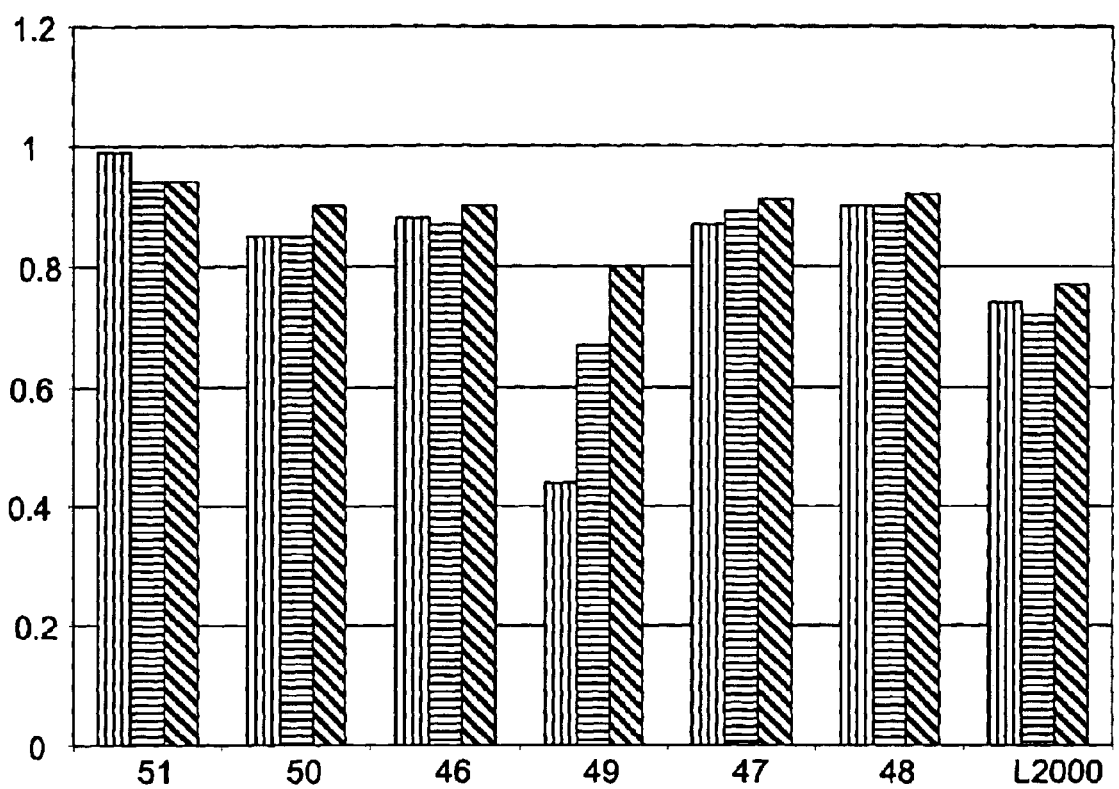
FIG. 5 shows a bar graph plotting cell viability (I=100%) of 293 cells for polyacetals 46–51 and Lipofectamine 2000

The cytotoxicities of polyacetals 46–51 on mammalian cells were evaluated using the 3-[4,5-dimethylthiazol-2-yl]-2,5-diphenyltetrazolium bromide (MTT) method. In this method, 96-well plates were seeded with 293 cells ($4 \times 10^4$ cells/well) and the cells incubated for 24 hours. Various amounts of the polyacetal-DNA complexes prepared as described in Example 52 were added to the cells and the cells were incubated in $CO_2$ incubator for 48 hours. 10 µl of MTT solution (5.0 mg/ml) was added to each well, and incubated for 3 hrs. The medium was then removed and 200-µl DMSO was added to dissolve the formazan crystals. The absorbance of the solution was measured at 570=m. Cell viabilities was calculated using the equation: Viability (%)= $\{Abs_{570(sample)}/Abs_{570(control)}\} \times 100$. All the experiments were conducted in triplicate. The results shown in FIG. 5 show that the polyacetals were less toxic to cells than Lipofectamine 2000.

EXAMPLE 56

Antisense oligo in vitro delivery: The Luciferase 705 gene system was developed by Dr. Kole at the University of Northern Carolina. In this system, the intron of human β-globin gene with mutation at 705 was inserted into the sequence between luciferase cDNA. This plasmid was introduced into HeLa cell for stable gene expression; the cell line was termed as HeLa luc705. Usually the cells exhibit low luciferase activity, because they express the wrong luciferase protein. However, the antisense oligo binding to the 705 sequence blocks the wrong splicing site in the 705 sequence and produces luciferase protein with biological activity. Luciferase 705 thus provides a functional model in antisense oligo delivery, with higher luciferase activity indicating higher efficiency of antisense delivery.

An 18 nt 2-O-methyl-phosphorothioate oligo nucleotide was obtained commercially from Midland Company. About 24 h before delivery, $1\times10^4$ HeLa luc705 cells/well was seeded in 96-well plate. The antisense oligo was diluted in 10 μl opti MEM (10 μmol/L), then different amounts of polyacetals 46–51 diluted in 10 μl opti MEM (640,320, 160 μg/ml) was added into the oligo solution dropwise while vortexing. The mixture was incubated at room temperature for 15 min to form oligo-polyacetal complexes. After that, the complexes were added into cells. The cells were incubated at 37° C. for 24 hours and luciferase activity was determined by luminometer. The background luciferase activity was about $1\times10^6$ RLU/mg in HeLa luc 705 cells. The results obtained for the transfection of Luc 705 cells with antisense oligo using polyacetals 46–51 and L2000 (positive control) are shown in FIG. 6. These results show that transfection efficiencies of polyacetals 46–51 are better than the current best commercial agent known, Lipofectamine 2000.

It will be appreciated by those skilled in the art that various omissions, additions and modifications may be made to the compositions and methods described above without departing from the scope of the invention, and all such modifications and changes are intended to fall within the scope of the invention, as defined by the appended claims.

What is claimed is:

1. A polymer comprising a recurring unit represented by a formula selected from the group consisting of formula (I) and (II):

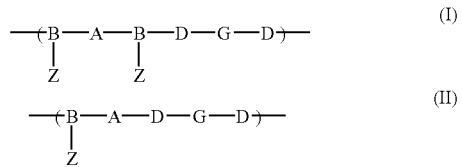

wherein A comprises at least one acetal group;
wherein B is selected from the group consisting of —CH—, —CH(CH$_3$)—, CH$_2$CH—, —CH$_2$C(CH$_3$)—, —CH(CH$_3$)CH—, and —CHCH(CH$_3$)CH(CH$_3$)—;
wherein Z is selected from the group consisting of C(O)OR$^1$, C(O)SR$^1$, C(O)NR$^1$R$^2$, and VU;
wherein V is a linker group;
wherein U is selected from the group consisting of poly(ethyleneimine), poly(propyleneimine), poly(lysine), PAMAM dendrimer, octaamine dendrimer, hexadecaamine dendrimer, enhancer, and targeting receptor;
wherein R$^1$ and R$^2$ are each individually selected from the group consisting of hydrogen, C$_1$ to C$_{10}$ alkyl, and C$_6$ to C$_{10}$ aryl;
wherein D is a linkage selected from the group consisting of carboxylic amide, carboxylic ester, urea, and urethane; and
wherein G is selected from the group consisting of C$_4$ to C$_{20}$ alkyl, C$_6$–C$_{10}$ aryl, and —(OCH$_2$CH$_2$)$_n$—, where n is in the range of 1 to about 250.

2. The polymer of claim 1 in which U is poly(ethyleneimine).

3. The polymer of claim 2 in which the poly(ethyleneimine) has a molecular weight in the range of about 200 to about 100,000 Daltons.

4. The polymer of claim 1 in which U is poly(lysine).

5. The polymer of claim 4 in which the poly(lysine) has a molecular weight in the range of about 200 to about 50,000 Daltons.

6. The polymer of claim 1 in which Z is VU.

7. The polymer of claim 2 in which V is —C(O)NH—.

8. The polymer of claim 1 in which U is selected from the group consisting of poly(ethyleneimine), enhancer, and targeting receptor.

9. The polymer of claim 8 in which U is a poly(ethylenimine) having a molecular weight in the range of about 200 to about 100,000 Daltons.

10. The polymer of claim 8 in which U is an enhancer selected from the group consisting of lipid, cholesterol, lipoprotein, fatty acid, lysosomotrophic agent, and fusogenic agent.

11. The polymer of claim 8 in which U is a targeting receptor selected from the group consisting of transferrin, antibody, antibody fragment, galactose, and mannose.

12. A method for making the polymer of claim 1, comprising reacting a monomer represented by a formula selected from the group consisting of formula (III) and formula (IV) with a comonomer having a formula represented by formula (V):

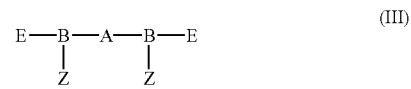

wherein A, B, Z and G have the same meanings as set forth in claim 1;
wherein E is selected from the group consisting of —OH, —NH$_2$, and —NH(CH$_3$); and
wherein C is selected from the group consisting of isocyanate, NHS-ester, carboxylic acid, carboxylic ester, carboxylic acid chloride and anhydride.

13. A method for making the polymer of claim 7, comprising reacting a compound represented by the formula H$_2$NU with a polymer comprising a recurring unit represented by a formula selected from the group consisting of formula (VII) and (VIII):

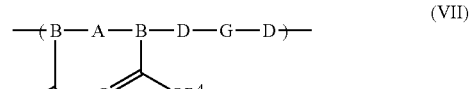
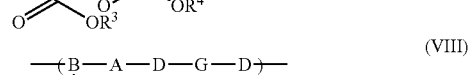

wherein U, A, B, D and G have the same meanings as set forth in claim 1; and wherein $R^3$, $R^4$ and $R^5$ are each individually selected from the group consisting of hydrogen, $C_1$ to $C_{10}$ alkyl, and $C_6$ to $C_{10}$ aryl.

14. A complex comprising the polymer of claim 6 and a polynucleotide.

15. A method for making the complex of claim 14, comprising intermixing the polymer of claim 6 and the polynucleotide.

16. The method of claim 15 in which the intermixing is conducted by adding a solution comprising the polymer of claim 6 to a second solution comprising the polynucleotide.

17. The method of claim 16 in which the V in the polymer of claim 6 is —C(O)NH—.

18. A method for transfecting a cell, comprising contacting the cell with the complex of claim 14.

19. The method of claim 18 in which the V in the polymer of claim 6 is —C(O)NH—.

20. The method of claim 19 in which the U in the polymer of claim 6 is poly(ethyleneimine).

21. The polymer of claim 1 in which the recurring unit is represented by a formula selected from the group consisting of formula (IX) and formula (X):

24. The polymer of claim 21 in which U is poly(lysine).

25. The polymer of claim 24 in which the poly(lysine) has a molecular weight in the range of about 200 to about 50,000 Daltons.

26. The polymer of claim 21 in which Z is VU.

27. The polymer of claim 26 in which V is —C(O)NH—.

28. The polymer of claim 21 in which U is selected from the group consisting of poly(ethylenimine), an enhancer, and targeting receptor.

29. The polymer of claim 28 in which U is poly(ethylenimine) having a molecular weight in the range of about 200 to about 100,000 Daltons.

30. The polymer of claim 28 in which U is an enhancer selected from the group consisting of lipid, cholesterol, lipoprotein, fatty acid, lysosomotrophic agent, and fusogenic agent.

31. The polymer of claim 28 in which U is a targeting receptor selected from the group consisting of transferrin, antibody, antibody fragment, galactose, and mannose.

32. A method for making the polymer of claim 21, comprising reacting a monomer represented by a formula selected from the group consisting of formula (XI) and formula (XII) with a comonomer represented by the formula (XIII):

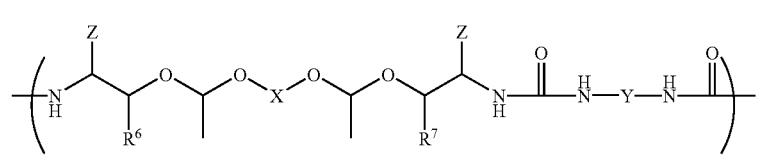

(IX)

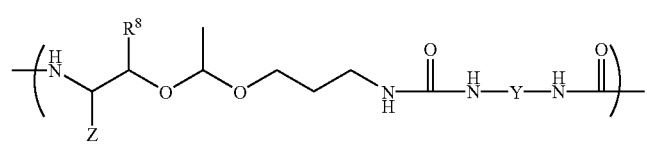

(X)

wherein Z has the same meaning as set forth in claim 1;

wherein $R^6$, $R^7$ and $R_8$ are each individually selected from the group consisting of H and —$CH_3$;

wherein X is selected from the group consisting of —$CH_2CH_2$—, —$CH_2CH_2CH_2CH_2$—, —$CH_2CH_2OCH_2CH_2$—, and —$CH_2CH_2OCH_2CH_2OCH_2CH_2$—; and wherein Y is selected from the group consisting of linear or branched $C_4H_8$, $C_5H_{10}$, $C_6H_{12}$, $C_7H_{14}$, $C_8H_{16}$, $C_{10}H_{20}$, and $C_{12}H_{24}$.

22. The polymer of claim 21 in which U is poly(ethylenimine).

23. The polymer of claim 22 in which the poly(ethylenimine) has a molecular weight in the range of about 200 to about 100,000 Daltons.

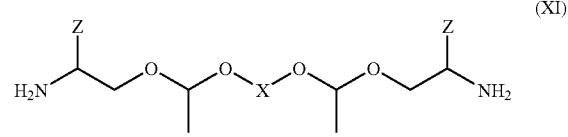

(XI)

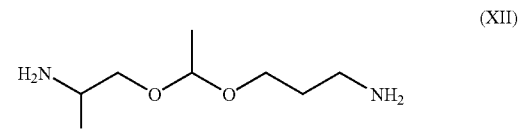

(XII)

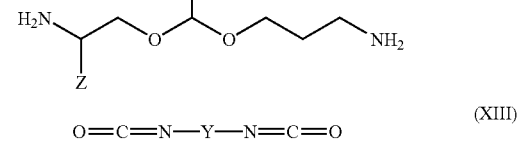

(XIII)

$O{=}C{=}N{-}Y{-}N{=}C{=}O$ wherein X, Y and Z have the same meanings as set forth in claim 21.

33. A method for making the polymer of claim 27, comprising reacting a poly(ethyleneimine) with a polymer comprising a recurring unit represented by a formula selected from the group consisting of formula (XIV) and formula (XV):

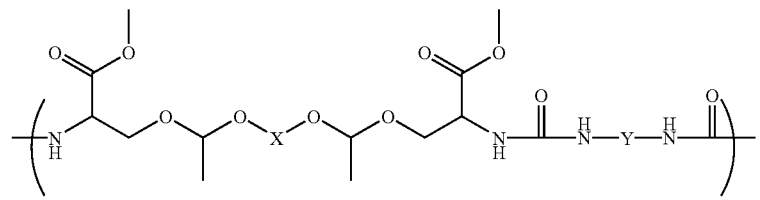

(XIV)

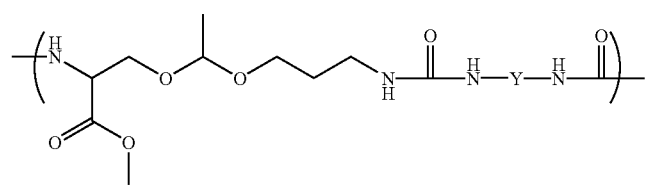

(XV)

wherein X and Y have the same meanings as set forth in claim 27.

34. A complex comprising the polymer of claim 26 and a polynucleotide wherein the polynucleotide is selected from the group consisting of plasmid DNA, antisense DNA, DNA oligomer, and siRNA.

35. A method for making the complex of claim 34, comprising intermixing the polymer of claim 26 and the polynucleotide.

36. The method of claim 35 in which the intermixing is conducted by adding a solution comprising the polymer of claim 26 to a second solution comprising the polynucleotide.

37. The method of claim 36 in which the V in the polymer of claim 26 is —C(O)NH—.

38. A method for transfecting a cell, comprising contacting the cell with the complex of claim 34.

39. The method of claim 38 in which the V in the polymer of claim 26 is —C(O)NH—.

40. The method of claim 39 in which the Z in the polymer of claim 26 is poly(ethyleneimine).

41. A monomer represented by a formula selected from the group consisting of formula (XI) and formula (XII):

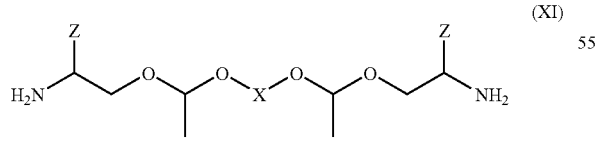

(XI)

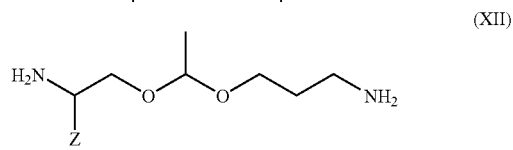

(XII)

wherein X is selected from the group consisting of —CH$_2$CH$_2$—, —CH$_2$CH$_2$CH$_2$CH$_2$—, —CH$_2$CH$_2$OCH$_2$CH$_2$—, and —CH$_2$CH$_2$OCH$_2$CH$_2$OCH$_2$CH$_2$—; and wherein Z is selected from the group consisting of C(O)OR$^1$, C(O)SR$^1$, and C(O)NR$^1$R$^2$, where R$^1$ and R$^2$ are each individually selected from the group consisting of hydrogen, C$_1$ to C$_{20}$ alkyl, and C$_6$–C$_{10}$ aryl.

42. A method for making the monomer of claim 41, comprising reacting a divinyl ether represented by formula (XVI) with about two equivalents of a compound represented by formula (XVII), in the presence of an acid in a non-alcoholic organic solvent:

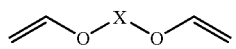

(XVI)

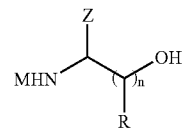

(XVII)

wherein X is selected from the group consisting of —CH$_2$CH$_2$—, —CH$_2$CH$_2$CH$_2$CH$_2$—, —CH$_2$CH$_2$OCH$_2$CH$_2$—, and —CH$_2$CH$_2$OCH$_2$CH$_2$OCH$_2$CH$_2$—;

wherein Z is selected from the group consisting of C(O)OR$^1$, C(O)SR$^1$, and C(O)NR$^1$R$^2$, where R$^1$ and R$^2$ are each individually selected from the group consisting of hydrogen, C$_1$ to C$_{20}$ alkyl, and C$_6$–C$_{10}$ aryl;

wherein M is a protecting group selected from the group consisting of 9-fluorenylmethyl carbamate, activated amide, and cyclic imide; and wherein R is methyl or hydrogen and wherein n is 1 or 2.

* * * * *